United States Patent
Bliss

(10) Patent No.: US 9,114,222 B2
(45) Date of Patent: Aug. 25, 2015

(54) PHASIC RESPIRATORY THERAPY

(75) Inventor: Peter Bliss, Prior Lake, GA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 785 days.

(21) Appl. No.: 13/131,628

(22) PCT Filed: Nov. 21, 2009

(86) PCT No.: PCT/IB2009/055251
§ 371 (c)(1),
(2), (4) Date: May 27, 2011

(87) PCT Pub. No.: WO2010/070492
PCT Pub. Date: Jun. 24, 2010

(65) Prior Publication Data
US 2011/0232638 A1    Sep. 29, 2011

Related U.S. Application Data

(60) Provisional application No. 61/122,905, filed on Dec. 16, 2008.

(51) Int. Cl.
*A61M 11/00* (2006.01)
*A61M 16/04* (2006.01)
*A61M 16/12* (2006.01)

(52) U.S. Cl.
CPC .............. *A61M 16/04* (2013.01); *A61M 16/042* (2013.01); *A61M 16/127* (2013.01)

(58) Field of Classification Search
CPC .. A61M 16/04; A61M 16/042; A61M 16/127
USPC .............. 128/204.21–204.23, 207.14–207.17
See application file for complete search history.

(56) References Cited

U.S. PATENT DOCUMENTS

| | | | | |
|---|---|---|---|---|
| 5,735,268 A | * | 4/1998 | Chua et al. | 128/204.23 |
| 7,051,736 B2 | * | 5/2006 | Banner et al. | 128/204.21 |
| 7,077,133 B2 | | 7/2006 | Yagi | |
| 7,588,033 B2 | * | 9/2009 | Wondka | 128/207.14 |
| 2004/0221854 A1 | | 11/2004 | Hete | |
| 2005/0005936 A1 | | 1/2005 | Wondka | |

FOREIGN PATENT DOCUMENTS

| | | |
|---|---|---|
| CN | 1552569 A | 12/2004 |
| JP | 2002085566 A | 3/2002 |
| JP | 2002513648 A | 5/2002 |
| WO | WO9956806 A1 | 11/1999 |
| WO | WO0056806 A1 | 9/2000 |
| WO | WO2008019102 A2 | 2/2008 |

* cited by examiner

*Primary Examiner* — Steven Douglas
(74) *Attorney, Agent, or Firm* — Michael W. Haas

(57) ABSTRACT

A respiratory therapy system that includes a gas delivery device enabled to deliver a quantity of oxygen-enriched gas and a quantity of insufflation gas is disclosed. The respiratory therapy system further provides a transtracheal catheter coupled to the gas delivery device. Additionally, the gas delivery device is enabled to deliver the quantity of insufflation gas during a first portion of a breathing cycle of a patient and to deliver the quantity of oxygen-enriched gas during a second portion of the breathing cycle.

9 Claims, 5 Drawing Sheets

PHASIC RESPIRATORY THERAPY

CROSS-REFERENCE TO RELATED APPLICATIONS

This patent application claims the priority benefit under 35 U.S.C. §119(e) of U.S. Provisional Application No. 61/122,905 filed on Dec. 16, 2008, the contents of which are herein incorporated by reference.

BACKGROUND OF THE INVENTION

1. Field of the Invention

The present invention relates generally to systems and methods for providing respiratory therapy and, more particularly, to systems and methods for providing phasic respiratory therapy.

2. Description of the Related Art

A growing number of people in the United States suffer from chronic obstructive pulmonary disease (COPD), such as asthma and emphysema, as well as cystic fibrosis, lung cancer, lung injuries, cardiovascular diseases, and otherwise diseased or damaged lungs. Although there is no cure for many of these conditions, their detrimental impact of can be mitigated by the prescription of respiratory therapy. The inhalation of respiratory therapy serves to compensate for the poor function of the patient's lungs in absorbing oxygen.

It can be appreciated that at the end of exhalation, not all of the exhaled gas containing $CO_2$, for example, is exhausted to atmosphere. A certain amount of exhaled gas remains in the physiological and anatomical dead space within the patient and in the structural dead space within the breathing circuit. It is generally desirable to prevent the exhaled, $CO_2$ laden gas in this dead space from being rebreathed by the patient, so that the patient receives the maximum amount of oxygen or other therapeutic gas and a minimal amount of $CO_2$ during each breath. In some patients, such as patients with cranial injuries, it is imperative that their $CO_2$ level not be elevated.

Tracheal gas insufflation (TGI) is one method that attempts to remove the exhaled gas from the physiological, anatomical and structural dead spaces in a patient being treated with a ventilator. Tracheal gas insufflation involves introducing an insufflation gas, such as oxygen, an oxygen mixture, or other therapeutic gas, into the patient's airway at the distal end of breathing circuit. In the embodiment illustrated in FIG. 1, an insufflation gas source 48, such as a pressurized tank or oxygen or an oxygen wall supply, delivers a flow of insufflation gas via a conduit 50 as a stream of gas into the patient's airway. Conduit 50 is also referred to as an "insufflation catheter." In a conventional TGI system, a proximal end of conduit 50 is coupled to insufflation gas source 48 through a control valve 52, and a distal end of conduit 50 is located generally within or near the distal end of endotracheal tube 30 so that the flow of insufflation gas is directed toward lungs 38, as indicated by arrow 54. Typically, the distal end of conduit 50 is located just above the patient's carina. The oxygen rich flow of insufflation gas discharged from the distal end of conduit 50 displaces the exhaled air in the anatomical and structural dead spaces so that the patient inhales the fresh (non $CO_2$ laden) gas on the next breath, thereby minimizing rebreathing of $CO_2$ to keep the patient's $CO_2$ levels as low a possible.

An alternative respiratory therapy augmentation technique is transtracheal augmented ventilation ("TTAV"). TTAV is the transtracheal delivery of high flows of a heated and humidified air/oxygen blend via a transtracheal catheter. TTAV is an advanced application of standard transtracheal oxygen ("TTO") in which relatively high flow rates are delivered to the patient through a transtracheal catheter. Because TTAV bypasses the upper airway, heat and humidity can be provided to prevent dessication of mucus and the potential for the development of mucus balls. TTAV can be a highly effective method of respiratory therapy as it can decrease the work of breathing. As described in U.S. Pat. No. 5,101,820 ("'820 patent"), transtracheal augmentation of ventilation can facilitate the removal of $CO_2$ and the resting of respiratory muscles. The '820 patent describes a TTAV system that includes a liquid oxygen tank 20, a source of oxygen, and a compressor 40, a source of air, connected to a blender 30. Blender 30 is then connected to a humidifier 70 that outputs the oxygen/air mixture to the patient through a tube connected to the patient's transtracheal catheter. The TTAV system of the '820 patent delivers a continuous flow of an oxygen/air mixture to the patient.

Although effective for their intended purposes, the conventional devices do not provide a flexible and convenient method of ventilation for a non-intubated patient. Thus, prior art devices can be inefficient in some implementations, and for some patients, in delivering respiratory therapy. Furthermore, prior art portable devices and home devices that provide efficient delivery of oxygen are unable to provide ventilation to the patient.

SUMMARY OF THE INVENTION

The present invention describes systems and methods to provide respiratory therapy. An exemplary embodiment of the present invention provides a respiratory therapy system including a gas delivery device enabled to deliver a quantity of oxygen-enriched gas and a quantity of insufflation gas. The respiratory therapy system further provides a transtracheal catheter coupled to the gas delivery device. Additionally, the gas delivery device is enabled to deliver the quantity of insufflation gas during a first portion of a breathing cycle of a patient and to deliver the quantity of oxygen-enriched gas during a second portion of the breathing cycle.

In addition to respiratory therapy systems, the present invention provides methods for respiratory therapy. An exemplary embodiment of a method for respiratory therapy includes determining an onset of an expiratory phase by a patient. After a predetermined delay period from the onset of the expiratory phase, the method for respiratory therapy includes the delivering a quantity of insufflation gas to the patient for a predetermined expiratory flushing period. Furthermore, after a predetermined expiratory flushing period, the method for respiratory therapy includes delivering a quantity of oxygen-enriched gas to the patient for a predetermined oxygen therapy period.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

The present invention addresses the deficiencies in the prior art concerning the inability of prior art respiratory therapy devices to efficiently and conveniently provide ventilation to a patient. Significantly, the present invention provides methods and apparatus for respiratory therapy involving the delivery of insufflation gas through a transtracheal catheter. A respiratory therapy system provided in accordance with the present invention is enabled to deliver insufflation gas to the patient and effectively deliver oxygen-enriched gas. Additionally, the present invention overcomes the drawbacks of the conventional methods and systems in the prior art and provides systems and methods enabled to provide ventilation within a portable respiratory device.

In an exemplary embodiment, the present invention provides a respiratory therapy system including a gas delivery device enabled to deliver a quantity of oxygen-enriched gas and a quantity of insufflation gas. The respiratory therapy system further provides a transtracheal catheter coupled to the gas delivery device. Additionally, the gas delivery device is enabled to deliver the quantity of insufflation gas during a first portion of a breathing cycle of a patient and to deliver the quantity of oxygen-enriched gas during a second portion of the breathing cycle.

In addition to respiratory therapy systems, the present invention provides methods for respiratory therapy. An exemplary embodiment of a method for respiratory therapy includes determining an onset of an expiratory phase by a patient. After a predetermined delay period from the onset of the expiratory phase, the method for respiratory therapy includes delivering a quantity of insufflation gas to the patient for a predetermined expiratory flushing period. Furthermore, after a predetermined expiratory flushing period, the method for respiratory therapy includes delivering a quantity of oxygen-enriched gas to the patient for a predetermined oxygen therapy period.

One of the significant advantages provided by respiratory therapy system in accordance with the present invention is the ability assist in ventilation. More particularly, a respiratory therapy system provided in accordance with the present invention has the ability to flush the anatomic deadspace of patient's breathing passageways and expel exhaled carbon dioxide ($CO_2$) from this deadspace. Typically, a patient must be placed on a ventilator to receive insufflation gas to aid in the dissipation of exhaled gas. The respiratory therapy system provided in accordance with present invention enables a non-intubated patient to gain the benefits of displacement of exhaled gas through insufflation. In an exemplary embodiment of the method of respiratory therapy enabled by the present invention, insufflation gas can delivered to the patient during a portion of the expiratory phase of the breathing cycle.

Figure 1:
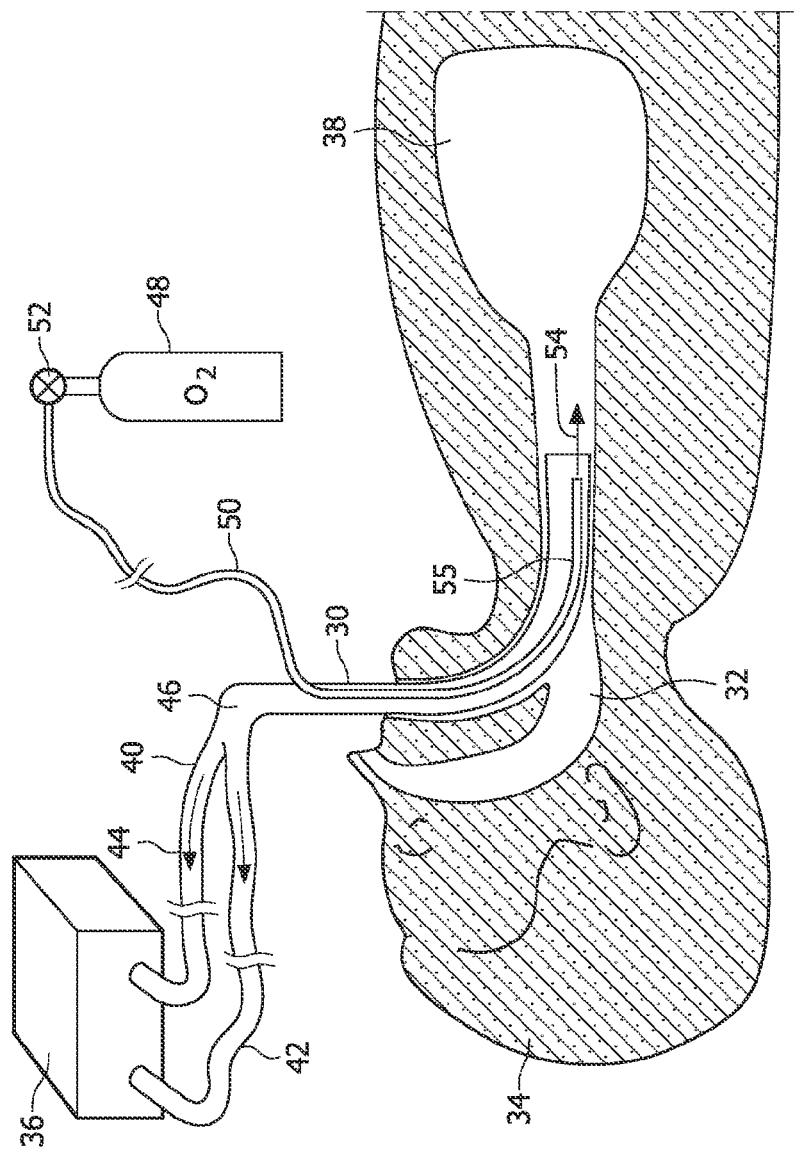
FIG. 1 illustrates an example of a conventional system, commonly referred to as a tracheal gas insufflation (TGI) system, in which a flow of insufflation gas is delivered to the airway of the patient.
Figure 2:
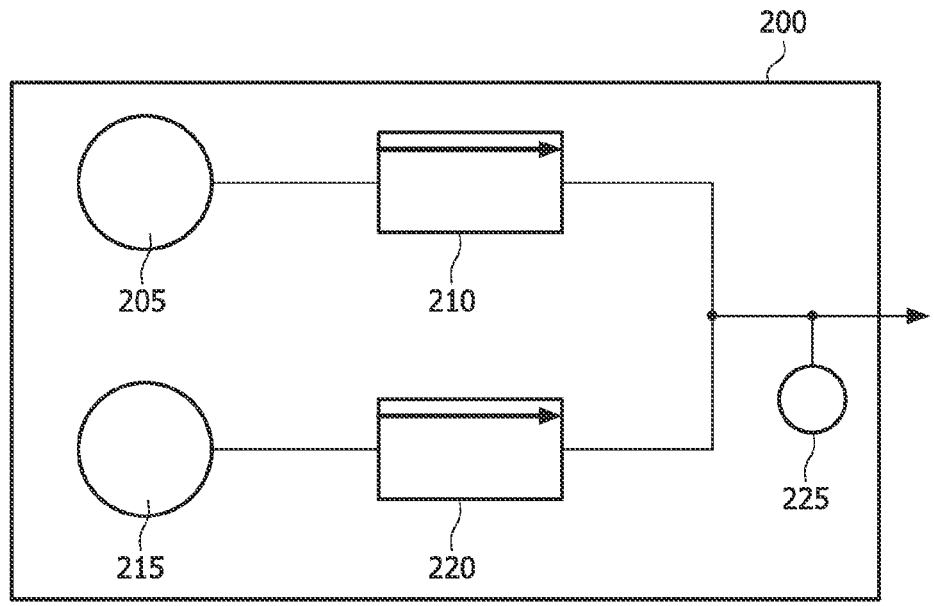
FIG. 2 provides a high-level block diagram of a respiratory therapy system 200 provided in accordance with an exemplary embodiment of the present invention.

FIG. 2 provides a high-level block diagram of a respiratory therapy system 200 provided in accordance with an exemplary embodiment of the present invention. As shown in FIG. 2, a respiratory therapy system 200 can include both an oxygen source 205 and an insufflation gas source 215 and can be enabled to deliver insufflation gas, typically air, to flush anatomic deadspace in a patient's breathing passageways and to deliver therapeutic oxygen. As shown in the exemplary embodiment in FIG. 2, respiratory therapy system 200 can further include an oxygen valve 210 to control the delivery of oxygen and an insufflation valve 220 to control the delivery of insufflation gas to the patient. These two valves, 210 and 220, permit oxygen-enriched gas and insufflation gas to be independently delivered to the patient. Furthermore, the exemplary embodiment of respiratory therapy system 200 shown in FIG. 2 can include a pressure transducer 225, or breath-sensing device, to trigger and control the delivery of oxygen-enriched gas and insufflation gas to the patient. A controller, not shown, can be used to control the operation of valves 210 and 220 to provide the therapy as described herein.

The pressure transducer, in an exemplary embodiment of respiratory therapy system 200, can be enabled to sense pressure changes in the delivery line to the patient and thereby sense the beginning of expiration, inspiration, or other changes in pressure. Those of skill in the art will appreciate that the pressure transducer 225 can be used in a variety of ways to provide a trigger for the phasic delivery of both insufflation gas and oxygen by various embodiments of respiratory therapy system 200.

Those of skill in the art will appreciate that pressure transducer 225 is one of many different suitable breath-sensing devices. In some embodiments, backpressure of gas flowing through the gas delivery tubing and transtracheal catheter of an alternative embodiment respiratory therapy system 200 can effectively mask the triggering pressure signal while gas is flowing. Therefore, in certain embodiments of the respiratory therapy system 200 it may be advantageous to include alternate methods for sensing the breathing pattern and triggering the flow of gas. For example, and not limitation, in an alternative embodiment of respiratory therapy system 200, the breath-sensing device can be an "effort belt" worn by the patient around the abdomen or chest. The "effort belt" device can be enabled to sense the expansion or contraction of the patient's thorax due to breathing. The output of the "effort belt" in an alternative embodiment of respiratory therapy system 200 can be a voltage signal which goes up and down with the movement of the patient's thorax. In the alternative embodiment, respiratory therapy system 200 can rely on this signal to determine the patient's breathing pattern. In addition to an "effort belt," those of skill in the art will appreciate that other possible breath-sensing methods could include thoracic impedance and nasal and/or oral cannula pressure.

In an exemplary embodiment, respiratory therapy system 200 is connected to a transtracheal catheter or other tracheal tube. The term transtracheal catheter is used herein to refer to any tube that crosses the trachea, or windpipe, that connects the upper respiratory tract and the lower respiratory tract. In an exemplary embodiment, the transtracheal catheter can be a 9 french flexible tube having a durometer of between 70 to 90 Shore A and an external diameter substantially less than the cross-sectional area of the patient's trachea, ranging from 3.5 mm or less.

An exemplary embodiment of respiratory therapy system 200 can effectively flush deadspace and deliver oxygen in a transtracheal embodiment. In one embodiment, insufflation gas source 215 can provide a quantity of gas made up primarily of air to flush the deadspace in the trachea and upper airway. Once the exhaled gas, including $CO_2$, is sufficiently displaced by the insufflation gas, this embodiment of respiratory therapy system 200 can independently deliver a quantity of oxygen-enriched gas to the patient. One significant benefit of the present invention over the prior art is that an exemplary embodiment of respiratory therapy system 200 can rely upon a smaller quantity of oxygen to provide respiratory therapy at level equivalent to a prior art device using a larger quantity of oxygen. By providing late expiratory insufflation gas for flushing followed by oxygen for oxygenation, an exemplary embodiment of respiratory therapy system 200 can minimize oxygen use and maximize ventilation with an more readily available insufflation gas such as air. Thus, respiratory therapy system 200 can consume less oxygen to achieve a equivalent level of patient oxygenation than a prior art device.

In an exemplary embodiment, insufflation source 215 can be a source of compressed air. In certain embodiments, respiratory therapy system 200 can include an air compressor to serve as insufflation source 215, thereby providing pressurized air for flushing purposes. The addition of an air compressor as an insufflation source 215 may be appropriate in respiratory therapy systems 200 in which oxygen source 205 is compressed oxygen or liquid oxygen. In an alternative embodiment, oxygen source 205 is an oxygen concentrator. In this alternative embodiment, insufflation source 215 can be implemented to rely upon compressor of the oxygen concentrator to provide a compressed insufflation gas source. In this alternative embodiment, insuffialtion source 215 is coupled to the oxygen concentrator compressor and receives compressed ambient air to be used as insufflation gas by system 200. Those of skill in the art will appreciate that there are numerous different configurations in which insufflation source 215 can be implemented to minimize the impact on oxygen production or consumption by the respiratory device.

Figure 3:
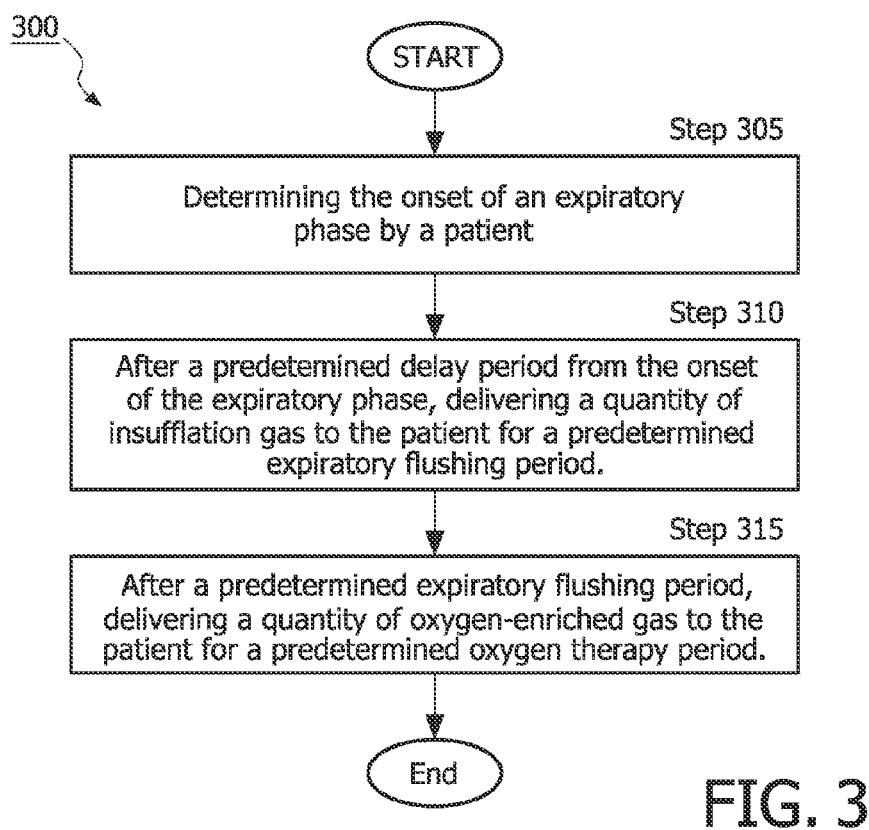
FIG. 3 provides a block diagram for the method of respiratory therapy provided in accordance with an exemplary embodiment of the present invention.

FIG. 3 is a block diagram illustrating a method of respiratory therapy 300 provided in accordance with an exemplary embodiment of the present invention. In an exemplary embodiment of the method of respiratory therapy 300, a more efficient and effective method of respiratory therapy is provided that flushes exhaled gas and delivers oxygen according to the breathing cycle of the patient. The term "breathing cycle" is used herein to refer to the combination of one inspiratory phase and one expiratory phase by a patient. Generally, not all of the gas exhaled by a patient during the expiratory phase of the breathing cycle is exhausted to the atmosphere. Thus, unwanted exhaled gas can remain in the patient's physiological and anatomical dead space and within the breathing circuit of the respiratory therapy device.

It is generally desired to prevent rebreathing of the exhaled gas, laden with $CO_2$, so that a maximum amount of therapeutic oxygen and a minimum amount of $CO_2$ is delivered to the patient. The method of respiratory therapy 300 provided in an exemplary embodiment of the present invention involves the delivery of an insufflation gas to the patient to aid in removing unwanted exhaled gas and aid in preventing rebreathing of exhaled gas. As shown in the exemplary embodiment of the method of respiratory therapy 300 shown in FIG. 3, a first step 305 involves determining an onset of an expiratory phase by a patient. By determining the onset of an expiratory phase of the patient, the method of respiratory therapy 300 is enabled to be carried out in sequence with the breathing cycle of the patient. Those of skill in the art will appreciate that determining the onset of an expiratory phase of the breathing cycle is just one of many possible triggers that can be used by the method of respiratory therapy 300 to sequence with the breathing cycle. In an alternative embodiment, the method of respiratory therapy 300 can be triggered by the onset of the inspiratory phase of the breathing cycle.

As shown in FIG. 3, an exemplary embodiment of the method of respiratory therapy 300 further includes a step 310 of delivering a quantity of insufflation gas to the patient after a predetermined delay period from the onset of an expiratory phase. The predetermined delay period can change from implementation to implementation and from patient to patient. Therefore, in an exemplary embodiment of the method of respiratory therapy 300, the quantity of insufflation gas is delivered after the patient begins to exhale. In this manner, the exemplary embodiment of method of respiratory therapy 300 can delivery insufflation gas to aid in removing gas exhaled by the patient, including $CO_2$, from the anatomical deadspace and help prevent rebreathing of exhaled gas.

The exemplary embodiment of method of respiratory therapy 300 shown in FIG. 3 further includes step 315 involving delivering a quantity of oxygen-enriched gas to the patient for a predetermined oxygen therapy period after a predetermined expiratory flushing period. Step 315, therefore can involve the delivery of oxygen during a portion of the inspiratory phase of the breathing cycle. Those of skill in the art will appreciate that the steps of an exemplary embodiment of the method of respiratory therapy 300 can be sequenced such that they correspond to the breathing cycle, thereby flushing with insufflation gas during a portion of expiratory phase and delivering therapeutic oxygen during a portion of the inspiratory phase.

Figure 4:
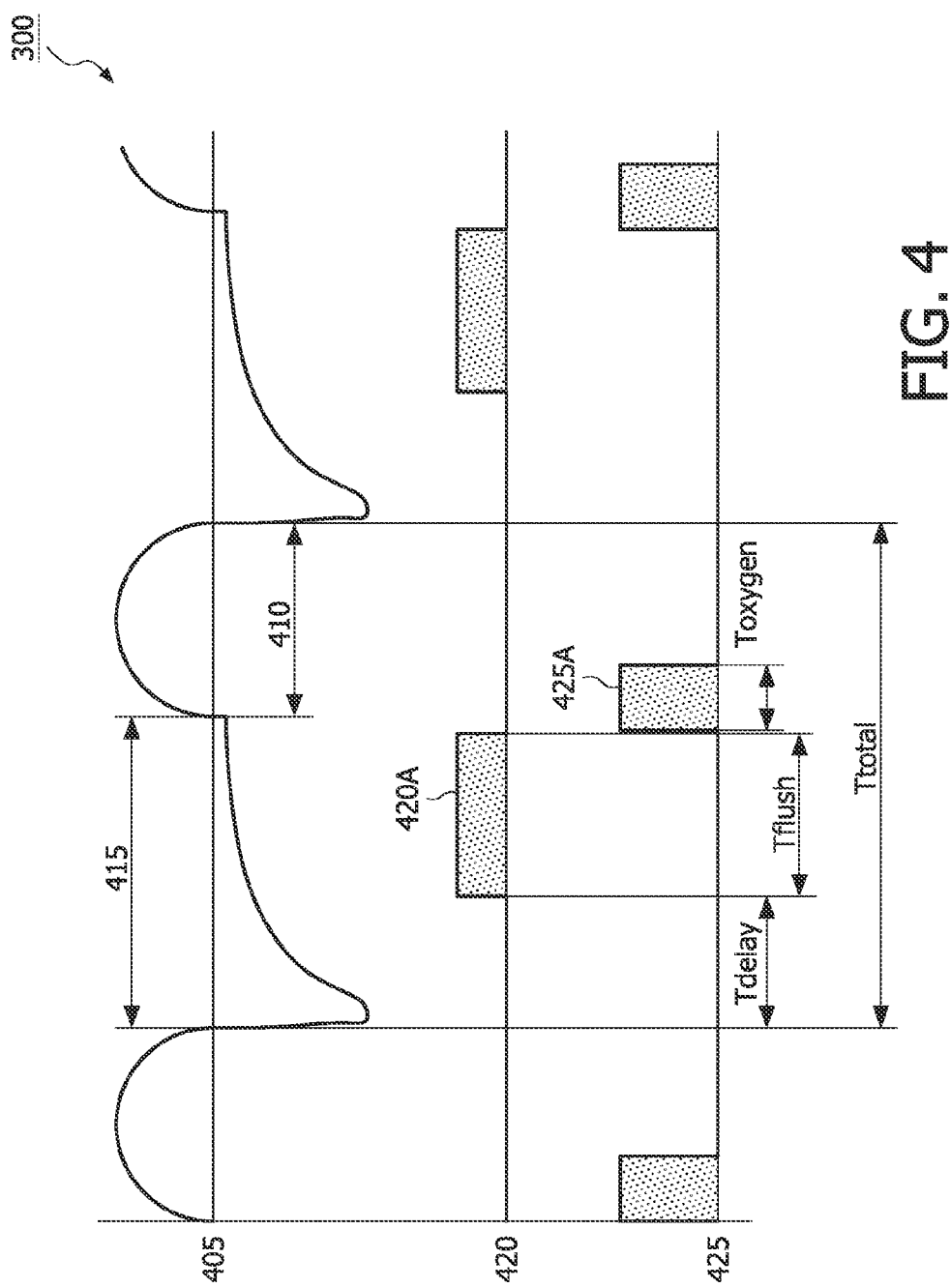
FIG. 4 provides a timing diagram for the method of respiratory therapy provided in accordance with an exemplary embodiment of the present invention.

FIG. 4 provides a timing diagram for the method of respiratory therapy 300 provided in accordance with an exemplary embodiment of the present invention. The diagram shown in FIG. 4 illustrates an example of breathing flow diagram of a breathing cycle 405 for a patient. As shown in FIG. 4, breathing cycle 405 illustrates an inhalation of gas during an inspiratory phase 410 and an exhalation of gas during an expiratory phase 415. In an exemplary embodiment, the method of respiratory therapy 300 uses this change in pressure from inspiratory phase 410 to expiratory phase 415 as a trigger. For example, and without limitation, in one embodiment, the onset of exhalation corresponds to an increase in the pressure in the catheter; thus time zero for an exemplary embodiment of the method of respiratory therapy 300 can established based on a sensing of this pressure change. Those of skill in the art will appreciate that this is just one example of a trigger and various embodiments of the method of respiratory therapy 300 can rely upon other triggers that occur in breathing cycle 405.

Once the trigger of the onset of expiratory phase 415 has been detected, constituting first step 305 of an exemplary embodiment of the method of respiratory therapy 300, second step 310 of delivering a quantity of insufflation gas to the patient can occur after a predetermined delay period. FIG. 4 illustrates the insufflation gas delivery 420 to the patient. As shown in the exemplary embodiment in FIG. 4, a quantity of insufflation gas 420A can be delivered to the patient after the predetermined delay period ("$T_{delay}$").

In an exemplary embodiment, $T_{delay}$ is the time from the onset of the expiratory phase 415 to the start of delivery of a quantity of insufflation gas 420A. $T_{delay}$ is calculated as a portion of one cycle ("$T_{total}$") of breathing cycle 405 or the time between the onset of first expiratory phase 415 and onset of second expiratory phase 415. $T_{total}$, one cycle of breathing cycle 405, can vary from person to person, ranging from 1 second for some people to 5 seconds for others, but typically having a length of around 3 seconds. For purposes of an exemplary embodiment of the method of respiratory therapy 300, $T_{total}$ is calculated as an average so as not to be offset by anomalies in the breathing cycle 405, such as a short breath or a long breath.

The filtered total value of $T_{total}$ (denoted "$T_{totalF}$") can be calculated in an exemplary embodiment as a running average or a low pass filter:

$$T_{totalF} = \frac{((T_{totalF} \times n) + T_{total})}{(n+1)}$$

where n is a constant that defines the speed of the filter and can range from 0 to 1000 (n=20 in an exemplary embodiment). Using $T_{totalF}$, $T_{delay}$ can defined as:

$$T_{delay} = T_{totalF} \times Z$$

where Z can be defined as a constant (typically in the range of 0 to 0.6) or can be calculated from the Inspiratory Fraction. The Inspiratory Fraction is the portion of the breathing cycle 405 spent on inhalation. The Inspiratory Fraction can be measured, fixed, or adjustable (in an exemplary embodiment the Inspiratory Fraction is around 0.33). The following defines the relationship between Z and the Inspiratory Fraction:

$$Z = (1 - \text{InspiratoryFraction}) \times V$$

where V is a constant ranging from 0 to 0.9, and in an exemplary embodiment V is 0.5.

In an exemplary embodiment of the method of respiratory therapy 300, the second step 310 of delivering a quantity of insufflation gas to the patient begins after $T_{delay}$ has expired. In an exemplary embodiment, the second step 310 can last for a predetermined expiratory flushing period ("$T_{flush}$"). $T_{flush}$ constitutes the time during which insufflation gas is delivered to expel exhausted gas from the anatomical deadspace of the patient to reduce inspiration of exhaled gas by the patient. As shown in FIG. 3, during $T_{flush}$ a quantity of insufflation gas 420A is delivered to the patient. $T_{flush}$ can be calculated as a function of $T_{totalF}$, described as:

$$T_{flush} = T_{totalF} \times Y$$

where Y can be either a constant ranging from 0.05 to 0.66 or can be calculated as follows:

$$Y = (1 - \text{InspiratoryFraction}) \times (1 - V)$$

Once a quantity of insufflation gas 420A is delivered for the predetermined expiratory flushing period ($T_{flush}$), the third step 215 of the exemplary embodiment of the method of respiratory therapy 300 is completed by delivering a quantity of oxygen-enriched gas 425A to the patient for a predetermined oxygen respiratory period ("$T_{oxygen}$"). $T_{oxygen}$ is the time period of the delivery of oxygen enriched gas during the breathing cycle 405. $T_{oxygen}$ is a function of the desired dose of oxygen and can vary based upon the patient and the oxygen prescription for that patient. Those of skill in the art will appreciate that $T_{oxygen}$ can vary depending upon a number of factors, including the desired dose, maximum flow rate, and delivery device. Toxgyen typically ranges from 0.1 seconds to 0.7 seconds. For example, and not limitation, $T_{oxygen}$ in an exemplary embodiment can be set to 0.24 seconds at a rate of 10 liters per minute (166 cc per second) and a desired dose of 40 mL.

As shown in diagram in FIG. 4, for every cycle of the breathing cycle 405, the method of respiratory therapy 300 can be implemented to deliver insufflation gas during an expiratory flushing period and to deliver oxygen during an oxygen respiratory period. Thereby, the system can enable more efficient and effective respiratory therapy. By flushing the anatomic deadspace of the patient, the method of respiratory therapy 300 can reduce the amount of exhaled gas that reenters the lungs and enable for more oxygen to be delivered for the alveolae during inspiration.

Figure 5:
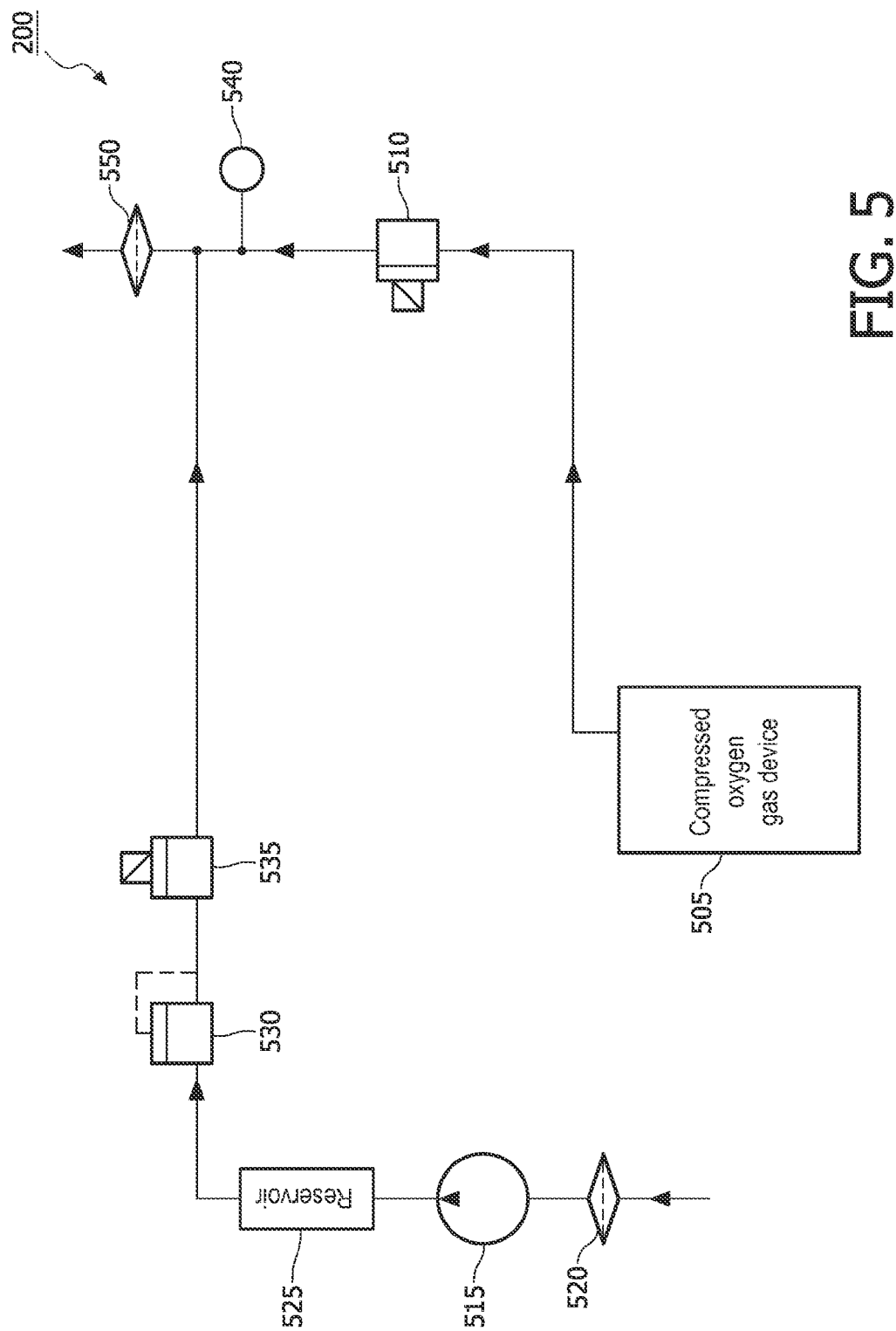
FIG. 5 provides a schematic of a respiratory therapy system implemented with an oxygen storage device provided in accordance with an exemplary embodiment of the present invention.

FIG. 5 provides a schematic of a respiratory therapy system 200 implemented with an oxygen storage device provided in accordance with an exemplary embodiment of the present invention. As shown in FIG. 5, respiratory therapy system 200 can be implemented in a liquid oxygen device or a compressed oxygen-enriched gas device. The exemplary embodiment of respiratory therapy system 200 shown in FIG. 5 can include a conventional liquid oxygen device or compressed oxygen-enriched gas device 505 coupled to an oxygen delivery valve 510 enabled to regulate the delivery of oxygen in an exemplary embodiment of respiratory therapy system 200.

A conventional liquid oxygen device 505 in one embodiment may be a stationary liquid oxygen device and in another embodiment the liquid oxygen device may be a portable liquid oxygen device. Similarly, a conventional compressed oxygen gas device 505 in one embodiment may be a stationary compressed oxygen gas device and in another embodiment the compressed oxygen gas device may be a portable compressed oxygen gas device. Respiratory therapy system 200 can provide an additional insufflation gas source, which is shown in an exemplary embodiment in FIG. 5 to be a compressor 515. Compressor 515 can coupled to an inlet filter 520 and thereby enabled to compress ambient air to be delivered for flushing purposes.

In some embodiments, respiratory therapy system 200 can be configured with an optional reservoir 525 to store a reserve of compressed insufflation gas. Additionally, some embodiments can be configured with an optional regulator 530 to regulate the flow of insufflation gas during flushing cycles. In the exemplary embodiment shown in FIG. 5, respiratory therapy system 200 includes a flush gas delivery valve 535, which can be controlled by a sensing and control circuit to deliver insufflation gas to the patient during the desired portion of the patient's breathing cycle. A pressure transducer 540 is configured in an exemplary embodiment of respiratory therapy system 200 to enable the sensing and control circuit to accurately trigger the delivery of either oxygen-enriched gas or insufflation gas during the desired portions of the patient's breathing cycle. An optional filter 550 is shown couple to the tubing communicating the flow of gas to the airway of the user.

One of the significant benefit's of the present invention, is that can enable portable oxygen devices to be more efficient. As shown in FIG. 5, respiratory therapy system 200 requires only a few components to be added to a conventional portable liquid or compressed oxygen device. In the exemplary embodiment shown in FIG. 5, respiratory therapy system 200 only adds a compressor 515, a flush gas delivery valve 535, and a pressure transducer 540 to the liquid oxygen device or compressed oxygen gas device 505. Therefore, a portable embodiment of respiratory therapy system 200 can provide both ventilation and oxygenation. This results in numerous potential benefits for the patient.

Figure 6:
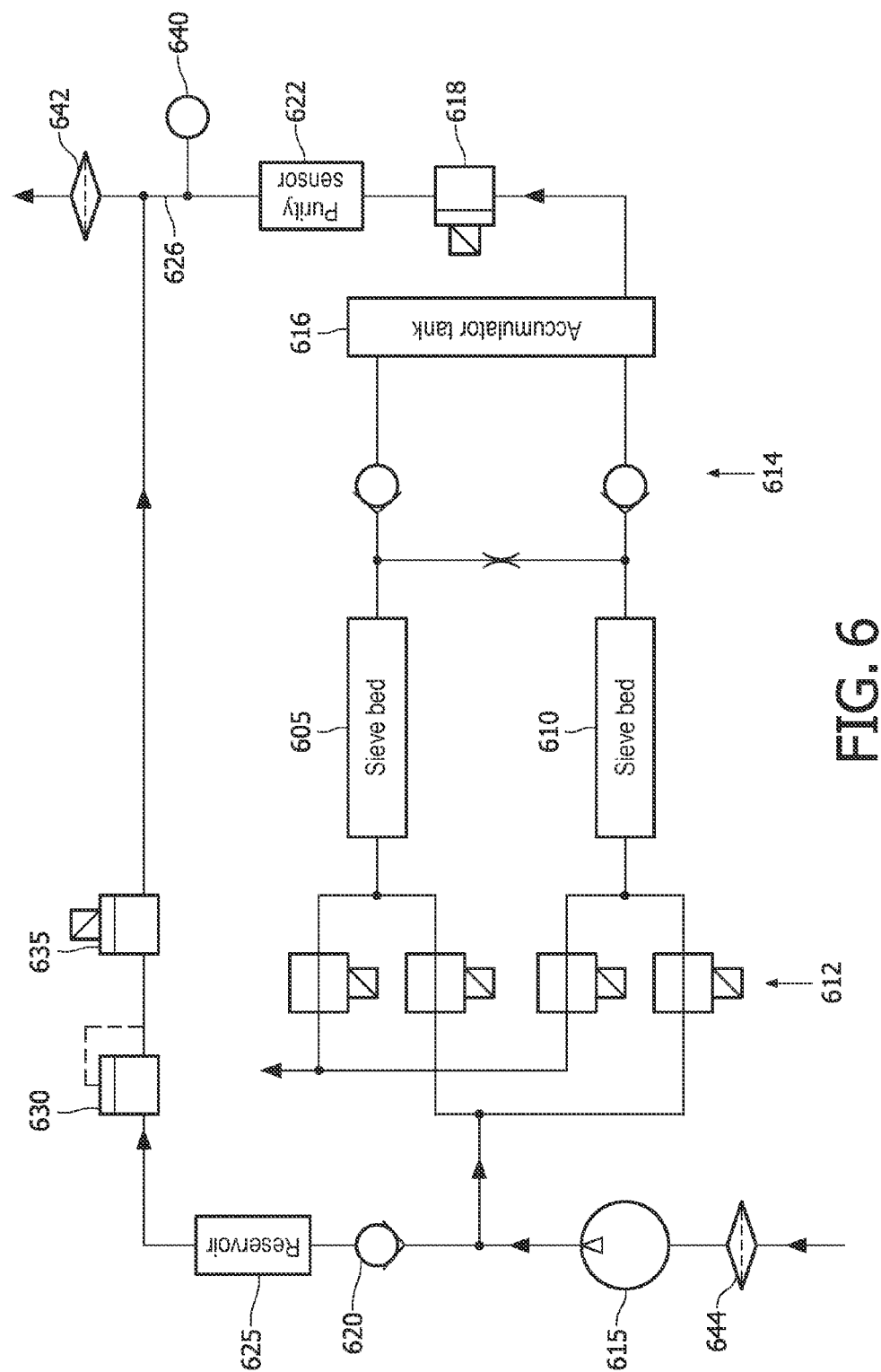
FIG. 6 provides a schematic of a respiratory therapy system implemented in oxygen concentrator device provided in accordance with an exemplary embodiment of the present invention.

FIG. 6 provides a schematic of a respiratory therapy system 200 implemented in oxygen concentrator device provided in accordance with an exemplary embodiment of the present invention. As shown in FIG. 6, respiratory therapy system 200 can be implemented in a oxygen concentrator device. The exemplary embodiment of respiratory therapy system 200 shown in FIG. 6 can include the conventional components of a oxygen concentrator system, such as two sieve beds, 605 and 610, purge control valves 612, check valves 614, a product accumulator tank 616, a flow control valve 618, a purity sensor 622, and a compressor 615. Thus, a first flow path 626 is provide for the flow of oxygen enriched gas to the patient. Compressor 615 is configured in an exemplary embodiment to provide compressed ambient air to sieve beds, 605 and 610, to enable the sieve beds to cycle sequentially from selective adsorption to desorption, thereby separating the oxygen from the ambient air. Respiratory therapy system 200 can be configured to rely upon compressor 615 to pressurize sieve beds, 605 and 610, as the insufflation gas source.

As shown in the schematic of the exemplary embodiment of respiratory therapy system 200 in FIG. 6, compressor 615 can be coupled by a check valve 620 to a secondary delivery path 628 to the patient. Thus, compressor 615 can provide a source of pressurized ambient air for use as the insufflation gas. In an exemplary embodiment, respiratory therapy system 200 can include an optional reservoir 625 to store the compressed ambient air to be used as insufflation gas. Additionally, some embodiments can be configured with an optional regulator 630 to regulate the flow of insufflation gas during flushing cycles.

In the exemplary embodiment shown in FIG. 6, the respiratory therapy system 200 includes a flush gas delivery valve 635, which can be controlled by a sensing and control circuit (not shown) to deliver insufflation gas to the patient during the desired portion of the patient's breathing cycle. A pressure transducer 640 is configured in an exemplary embodiment of respiratory therapy system 200 to enable the sensing and control circuit to accurately trigger the delivery of either oxygen-enriched gas or insufflation gas during the desired portions of the patient's breathing cycle. In the illustrated embodiment, first flow path 626 and second flow path 628 are combined so that the gas carried by each flow path can be delivered to the airway of a patient. An optional filter 642 can be provided to filter the gas prior to delivery to the patient. The present invention also contemplates providing an inlet filter 644 to filter the gas provided to the inlet of compressor 615.

Those of skill in the art will appreciate that the exemplary embodiment of the respiratory therapy system 200 shown in FIG. 6 can be a portable oxygen concentrator system or a stationary oxygen concentrator system. One of the significant benefit's of the present invention, is that can enable oxygen concentrator devices to be more efficient. As shown in FIG. 6, respiratory therapy system 200 requires only a few components to be added to a conventional oxygen concentrator device. In the exemplary embodiment, respiratory therapy system 200 can be configured to essentially only add a secondary output to the patient enabled to deliver pressurized ambient air to be used as insufflation gas. Therefore, a portable embodiment of respiratory therapy system 200 can provide both ventilation and oxygenation. This is significant for portable oxygen concentrator devices as it permits the systems to be relatively small, and therefore more lightweight and user friendly.

It can be appreciated from the foregoing that the present invention provides a method for providing phasic ventilation via a transtracheal catheter, as well as an apparatus and method for the phasic delivery of insufflation gas enabled to be synchronized with a patient's breathing cycle. The present invention further provides an apparatus and method for the phasic delivery insufflation gas with in-home or portable oxygen delivery devices Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory therapy system comprising:
   a gas delivery device enabled to deliver a quantity of oxygen-enriched gas and a quantity of insufflation gas;
   a transtracheal catheter coupled to the gas delivery device;
   a sensor configured to detect an onset of an expiratory phase of a breathing cycle; and
   a controller configured to control the gas delivery device to deliver the quantity of insufflation gas during a first portion of a breathing cycle of a patient and to deliver the quantity of oxygen-enriched gas during a second portion of the breathing cycle, wherein the first portion begins after a predetermined delay from the onset of the expiratory phase of the breathing cycle and wherein the first portion ends after a predetermined expiratory flushing period.

2. The respiratory therapy system of claim 1, wherein the sensor comprises a pressure transducer.

3. The respiratory therapy system of claim 1, wherein the second portion begins after the predetermined expiratory flushing period and wherein the second portion ends after a predetermined oxygen therapy period.

4. The respiratory therapy system of claim 1, wherein the gas delivery device includes a housing; wherein an insufflation gas source is coupled to the housing and enabled to deliver a quantity of insufflation gas to a patient; wherein an oxygen-enriched gas source is coupled to the housing and enabled to deliver a quantity of oxygen-enriched gas to the patient; and wherein the respiratory therapy system is portable.

5. The respiratory therapy system of claim 4, wherein an insufflation gas source of the gas delivery device includes a compressor enabled to provide a quantity of compressed ambient air.

6. The respiratory therapy system of claim 4, wherein an oxygen-enriched gas source of the gas delivery device is an oxygen concentrator device.

7. A method of respiratory therapy comprising:
   determining an onset of an expiratory phase of a breathing cycle of a patient with a sensor cofigured to detect an onset of an expiratory phase of a breathing cycle;
   after a predetermined delay period from the onset of the expiratory phase, control a gas delivery device to deliver a quantity of insufflation gas to the patient for a predetermined expiratory flushing period; and
   after a predetermined expiratory flushing period, control the gas delivery device to deliver a quantity of oxygen-enriched gas to the patient for a predetermined oxygen therapy period.

8. The method of respiratory therapy of claim 7, wherein the sensor configured to detect the onset of the expiratory phase of the breathing cycle comprises a pressure transducer.

9. The method of respiratory therapy of claim 7, wherein the quantity of insufflation gas and the quantity of oxygen-enriched gas are delivered to the patient via a transtracheal catheter.

\* \* \* \* \*